(12) United States Patent
Millar

(10) Patent No.: US 6,398,738 B1
(45) Date of Patent: Jun. 4, 2002

(54) METHOD AND APPARATUS FOR RECONSTRUCTING A HIGH FIDELITY PRESSURE WAVEFORM WITH A BALLOON CATHETER

(75) Inventor: Huntly D. Millar, Houston, TX (US)

(73) Assignee: Millar Instruments, Inc., Houston, TX (US)

( * ) Notice: Subject to any disclaimer, the term of this patent is extended or adjusted under 35 U.S.C. 154(b) by 45 days.

(21) Appl. No.: 09/668,912

(22) Filed: Sep. 25, 2000

(51) Int. Cl.⁷ ............................................... A61B 05/00
(52) U.S. Cl. ...................................................... 600/486
(58) Field of Search .................................. 600/486, 488, 600/487

(56) References Cited

U.S. PATENT DOCUMENTS 4,601,706 A * 7/1986 Aillon ......................... 600/486
5,113,868 A * 5/1992 Wise et al. .................. 600/486
5,755,668 A * 5/1998 Itoigawa et al. ............. 600/488

\* cited by examiner

*Primary Examiner*—Robert L. Nasser
(74) *Attorney, Agent, or Firm*—Thompson & Knight, LLP

(57) ABSTRACT

The invention provides a method and system for reconstructing a high-fidelity pressure waveform with a balloon catheter used in a heart. First, a balloon catheter having an air line is inserted into the aorta of the heart. The air line is then closed and sufficient air is introduced in order to equalize the pressure in the balloon catheter and the aorta. The AC components of the aortic pressure and the mean aortic pressure are detected separately and then added to form a high-fidelity pressure waveform. The high fidelity pressure waveform may be displayed on an oscilloscope, a patient monitor, or other suitable display.

13 Claims, 6 Drawing Sheets

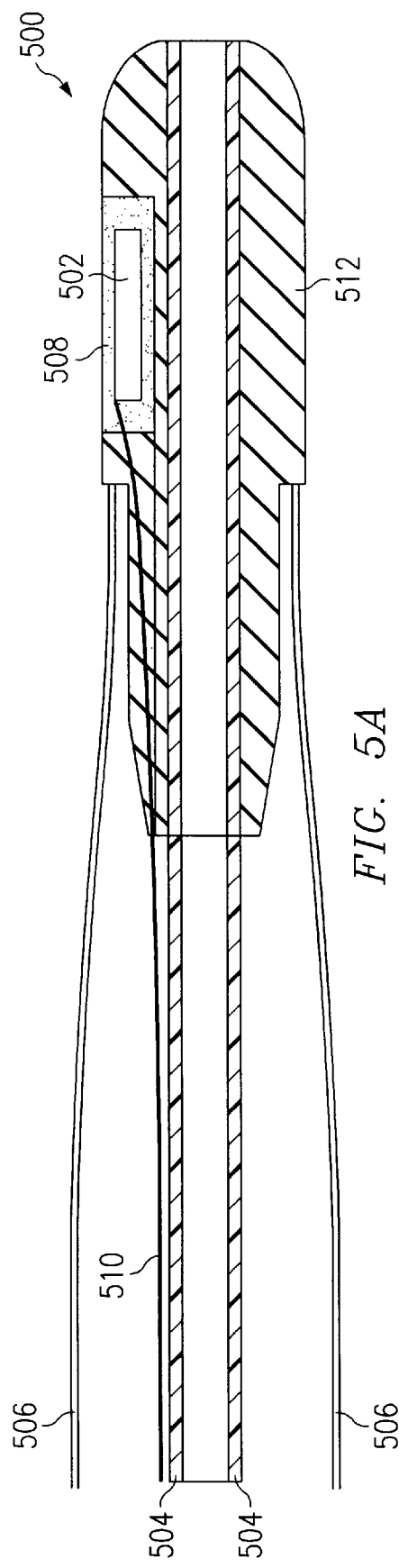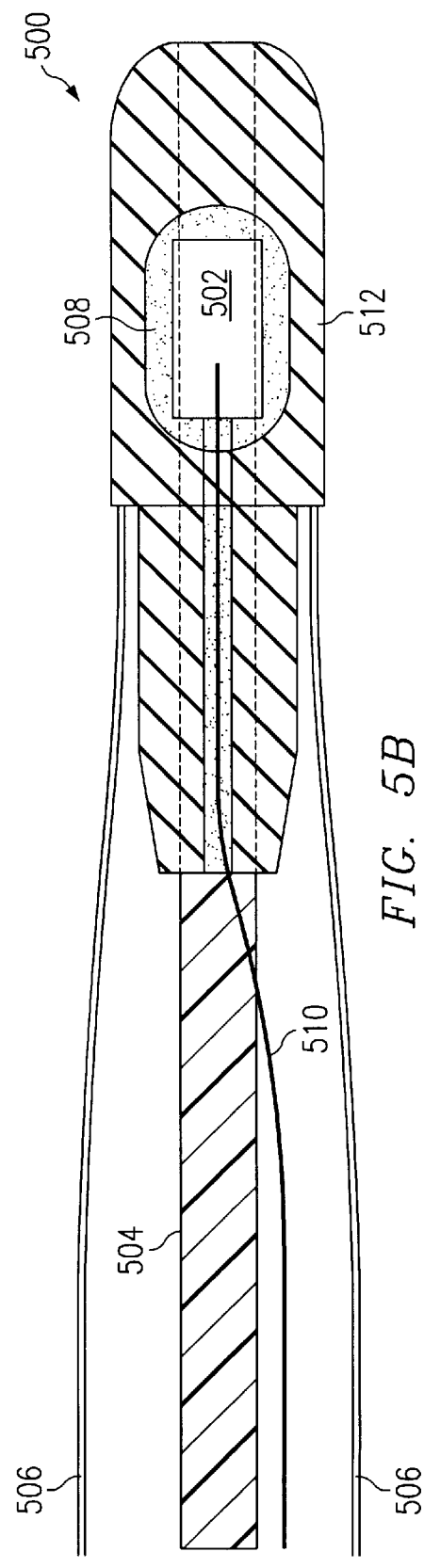
FIG. 5A
FIG. 5B

METHOD AND APPARATUS FOR RECONSTRUCTING A HIGH FIDELITY PRESSURE WAVEFORM WITH A BALLOON CATHETER

FIELD OF THE INVENTION

The invention relates to a method and apparatus for using reduced sized measurement devices with balloon assist catheters. In particular, the invention relates to an improved method and apparatus for controlling the inflation of a balloon assist catheter by using a pressure sensor to determine when to inflate and deflate the balloon to obtain maximum circulation effects.

Moreover, the invention relates to a method and apparatus for measuring mean blood pressure using a cardiac assist balloon catheter. In particular, this aspect of the invention relates to an improved method and apparatus for detecting mean pressure and using that measurement to reconstruct a high fidelity blood pressure waveform.

BACKGROUND OF THE INVENTION

Catheter tip measurement devices are catheters that have measurement sensors located at or near their distal tips. These devices are used in a variety of applications to measure internal properties of internal tissues and fluids such as blood volume, velocity, and pressure. Catheter tip measurement devices may be introduced directly into arteries, veins, or other body organs either by themselves or through other catheters that have been previously positioned within a patient. Catheter tip measurement devices generally have electrical or fiber optic connectors at the proximal end of the catheter that communicate data from the measurement sensors to external processing devices. One type of catheter tip measurement device is a catheter tip pressure transducer, which has at least one pressure transducer located at or near the distal tip of the catheter.

The size of the catheter tip is important, and for many applications, this size is the primary limiting factor that determines whether a measurement catheter may be used in a particular application. For example, size is important and is a limiting factor in measuring pressure within small vessels, such as coronary arteries. Size is also important where a catheter tip measurement device is being introduced through the lumen of another catheter. One such application is where a small sized catheter tip pressure transducer is introduced through the lumen of an electrode or conductance catheter. A conductance catheter has electrodes disposed at the distal end of the catheter to measure the resistivity of the blood, thereby determining the heart chamber volume. These measurements can be translated into volume and impedance measurements of heart segments on a beat-by-beat basis. A catheter tip pressure transducer introduced through the lumen of a conductance catheter allows for simultaneous measurement of pressure at the tip of the conductance catheter. In this way, the conductance catheter can be used for volume measurements, and the catheter tip pressure transducer can be used for pressure measurements. The resulting pressure/volume loops are of significant diagnostic value in many types of heart disease.

Present small-size catheter devices capable of making internal pressure measurements take the form of fluid-filled devices, electrical strain gauge type transducer devices, and fiber optic devices. Fluid-filled devices may have very small construction, but such devices provide poor measurement fidelity. Similarly, fiber optic devices may have a very small sensor size, but such devices have relatively unstable and unacceptable performance. In contrast, strain gauge type transducer devices, which utilize semiconductor pressure transducers, provide high-fidelity measurements but suffer from requiring a significantly larger feature size.

In addition to catheters with pressure transducers and other measurement devices at their distal tip, guidewires exist with measurement devices at their tip. Guidewires may be inserted into body organs and used to guide the insertion of a variety of catheters into the human body. Often catheters are too large and bulky to introduce them directly into arteries, veins, or other body organs. Therefore, smaller, more flexible guidewires are introduced into the body. Then, a catheter is slipped over the guidewire for insertion. The guidewire guides the catheter into the artery, vein, or body organ.

Guidewires may also be used to exchange catheters into arteries, veins, and body organs (referred to as "exchange guidewires"). When a catheter must be removed and replaced, an exchange guidewire is inserted through the lumen of the catheter. The catheter is then removed, leaving the guidewire in place. The replacement catheter may then be inserted by slipping it over the existing guidewire. When a guidewire with measurement devices at the distal tip includes external equipment associated with the measurement device, it is necessary to include a connector between the guidewire and the equipment. This connector allows the external equipment to be removed from the guidewire in order to permit the exchange of catheters.

Some guidewires include measurement devices at the distal tip. However, these guidewires either do not have very small construction because of the use of the pressure sensor at the distal tip, or they lack the measurement accuracy and stability required for most applications. For example, U.S. Pat. No. 4,941,473 illustrates a guidewire with a pressure sensor at the distal end of the guidewire. The guidewire comprises an optical fiber surrounded by a helically wound metal wire. The thickness of the helically wound metal wire and the tightness of the winding determine the torsional stiffness of the guidewire. Although this construction may allow for small feature sizes, it does not provide the measurement accuracy and stability required for most applications. In particular, this guidewire uses optical fibers to connect a pressure sensor to its associated measurement equipment. This device expands and distorts when inserted into the body due to temperature variations, causing a zero level shift in the measured pressure.

Another potential application for pressure measurement devices is with balloon assist catheters. Balloon assist catheters are flexible polyurethane bladders used to assist the heart with circulating blood through the body. FIG. 1 illustrates a human heart. In operation, a balloon assist catheter would be inserted through the femoral artery, fed through the artery, and placed approximately just below the aortic notch 5 within the aorta 4. The aorta 4 is the primary artery for delivering blood from the heart 2 to the systemic circulation system. Once in position, the balloon assist catheter is ideally inflated with helium immediately after the aortic valve 6 closes. When the balloon is inflated, the aortic diastolic pressure is increased and blood is pushed through the aorta 4 away from the heart 2. As the aortic valve opens, the balloon deflates rapidly, producing a decrease in aortic systolic pressure with a consequent decrease in resistance when the left ventricle 8 attempts to pump blood through the systemic circulation system. By inflating and deflating the balloon as described, which is referred to as counterpulsation, circulation of blood through the body may be improved. For a more complete discussion of the operation and use of intraaortic balloons, see CARDIAC CATHETERIZATION AND ANGIOGRAPHY, 3rd ed., Lea and Febiger, at pp. 493–501.

The inflation and deflation cycle lasts for approximately 225 milliseconds and timing of the cycle is critical to obtain maximum circulatory effect. If balloon inflation occurs too early, backflow of blood may occur into the heart. Likewise, if balloon inflation occurs too late, maximum circulation effects may not be obtained.

Traditionally, timing of the inflation of the balloon has been done by a human operator based on an electrocardiogram as shown in FIG. 2. The electrocardiogram (ECG) provides a graphic recording of the electrical manifestations of the heart action as obtained from the body surfaces. The ECG has three predominant wave forms, commonly known as the P wave, representing atrial depolarization; the QRS complex, representing ventricular depolarization, which is coincident with contraction of the ventricles; and the T wave, representing ventricular repolarization. Ventricular contraction occurs during the ST segment, but there is no precise electrical event coincident with aortic valve closure. Therefore, an operator trying to time balloon inflation by the ECG would have to estimate a number of milliseconds after ventricular contraction (corresponding to the ST segment) to inflate and deflate a balloon. However, this method of timing fails to provide accurate timing for balloon inflation due to human error. Additionally, because the duration of the mechanical contraction event may vary considerably from beat-to-beat, other inaccuracies are introduced.

An alternate method for timing the inflation of the balloon involves using external pressure transducers to identify the closure of the aortic valve 6. As shown in FIG. 2, the second heart sound in each cycle occurs when the ventricles relax and the valves shut. When this occurs, the aorta 4 is at a high pressure and the ventricle 8 is at a low pressure. As a result of these pressure differences, blood in the aorta 4 will rush slightly backwards and slam against the aortic valve, causing vibrations (i.e., creating pressure waves that may be detected). These momentary changes in pressure that occur when the valves shut create what is known as the dicrotic notch in the aortic pressure waveform. To detect these pressure changes, an external pressure transducer can be used to identify the dicrotic notch on the aortic pressure wave form (FIG. 2). Although the use of external pressure transducers has provided some improved timing of the balloon inflation, this method suffers from problems typically associated with external pressure transducers. These problems include imprecise timing due to fluid column linkage, time delay, and poor frequency response of the pressure transducers.

Pressure sensors have also been provided at the tip of a catheter. However, these sensors suffer from some of the same problems associated with external sensors. Additionally, these sensors directly monitor pressure levels and inherently suffer from an inability to maintain long term stability of DC pressure levels. For example, variations in temperature may result in inaccurate pressure measurements due to a zero level shift in the measured pressure. Although methods exist for maintaining long term stability, the stability may be attained only at considerable expense.

Therefore, a need has arisen for a method and apparatus for accurately timing the moment when the aortic valves close. Based on this measurement, a balloon catheter can be timely inflated to provide maximum circulation effects. Specifically, a need has arisen for more precisely timing the dicrotic notch with an aortic pressure sensor. In particular, a need has arisen for a method and apparatus for accurately measuring at the tip of a balloon catheter any pressure changes associated with the dicrotic notch.

Further, a need has arisen for a method and apparatus for accurately timing the moment when the aortic valve closes that is not affected by the long-term stability of the pressure sensor.

When timing the dicrotic notch in a balloon-assist catheter, the pulse waveform is the important information required for timing the inflation of the balloon catheter. Mean blood pressure in the heart can be evaluated independently and the pulse tracing itself used for timing purposes. However, in some instances, detection of the aortic pulse wave tracing may be insufficient. Some applications require accurate high-fidelity detection of the blood pressure waveform. For example, during balloon assist therapy, an operator may desire to alter the amount of air inflating the balloon. Alternatively, the operator may wish to alter the cycle of the therapy by inflating the balloon every other heartbeat or every third heartbeat. With each of these alterations, the operator would like to measure any corresponding changes in the central blood pressure in order to evaluate the necessary adjustments.

The use of catheter-tip pressure transducers provides excellent results for detecting the blood pressure waveform; however, as previously discussed, these types of transducers suffer from an inability to maintain long-term stability of DC pressure levels. A baseline pressure must be verified from time-to-time and a correction made to compensate for any drift.

Traditionally, a baseline pressure could be measured with a fluid-filled catheter or a balloon catheter connected to an external transducer. Although these methods are capable of transmitting a mean pressure, these methods tend to distort the pulsatory pressure waveform, which may not be suitable for systems that require high-fidelity waveform detection.

Therefore, a need has arisen for a method and apparatus for accurately timing the dicrotic notch with an aortic pressure sensor while maintaining the ability to reconstruct an accurate high-fidelity blood pressure waveform. More specifically, a need exists for a method and apparatus for accurately detecting a mean blood pressure tracing and reconstructing an accurate high-fidelity blood pressure waveform using a pressure sensor at the tip of a balloon catheter.

SUMMARY OF THE INVENTION

The present invention achieves these goals with a unique and advantageous structure for a pressure measurement device that provides the desired measurement capability. In particular, the present invention relates to a balloon catheter for use within a human body. The balloon catheter includes a support surface at the distal end of the catheter body for supporting a pressure measurement device. An inflatable balloon surrounds at least a portion of the catheter body. A pressure sensor is capacitively coupled to a detection circuit for removing DC bias and detecting frequency changes occurring at the pressure sensor.

In a specific embodiment, the pressure sensor is a semiconductor pressure sensor. In another specific embodiment, the pressure sensor is a fiber optic pressure transducer.

In another embodiment, the present invention is a system for detecting the aortic pressure in an aorta. The system includes a balloon catheter and a guidewire. The guidewire inserts through the lumen of the balloon catheter and includes a body and a support surface for supporting a measurement device. A capacitively coupled detection circuit is attached to the measurement device and removes DC bias and detects frequency changes occurring at the pressure sensor.

In yet another embodiment of the present invention, the present invention is a method for improving the circulation effects of a balloon catheter used in a heart. First, a balloon catheter is inserted into the aorta of the heart. Then, aortic pressure changes are measured near the heart. When the location of the dicrotic notch in the aortic pressure is determined by detecting the AC component of the measured aortic pressure changes, the balloon is inflated.

In yet another aspect, the present invention provides a method and apparatus for improving the circulation effects achieved by using a balloon catheter while maintaining the ability to accurately detect the mean pressure. Specifically, a system is provided for reconstructing a high-fidelity waveform of the blood pressure in the aorta of a human body using a balloon catheter. The catheter body has a proximal end and a distal end with a support surface to support a pressure measurement device. A capacitively coupled detection circuit is connected to the pressure sensor for removing DC bias and detecting frequency changes occurring at the pressure sensor. An external pressure transducer located at one end of the catheter body detects the mean pressure within the inflatable balloon. The system may also include a patient monitor for displaying the high-fidelity waveform by adding the output of the capacitively coupled detection circuit and the output of the external pressure transducer. Alternatively, the system may use an oscilloscope or a computer to add and display the components of the high-fidelity waveform.

In an embodiment, the system may be used to detect frequency changes corresponding to the dicrotic notch in the aortic pressure. The detection of the dicrotic notch may be used to accurately time when to inflate the balloon catheter.

In yet another embodiment, the invention provides a method for reconstructing a high-fidelity pressure waveform with a balloon catheter used in a heart. First, a balloon catheter having an air line is inserted into the aorta of the heart. The air line is then closed and sufficient air is introduced in order to equalize the pressure in the balloon catheter and the aorta. The AC components and the mean aortic pressure are detected separately and then added to form a high-fidelity pressure waveform. The method may be performed using a disposable pressure sensor. The high fidelity pressure waveform may be displayed on an oscilloscope, a patient monitor, or other suitable display.

BRIEF DESCRIPTION OF THE DRAWINGS

For a more complete understanding of the present invention and the advantages thereof, reference is now made to the following description taken in conjunction with the accompanying drawings. In the drawings, depicted elements are not necessarily drawn to scale and like or similar elements may be designated by the same reference numeral throughout the several views.

FIGS. 5A and 5B illustrate a side view and a top view of the tip of a balloon catheter incorporating the pressure sensor of the present invention.

DETAILED DESCRIPTION

Figure 1:
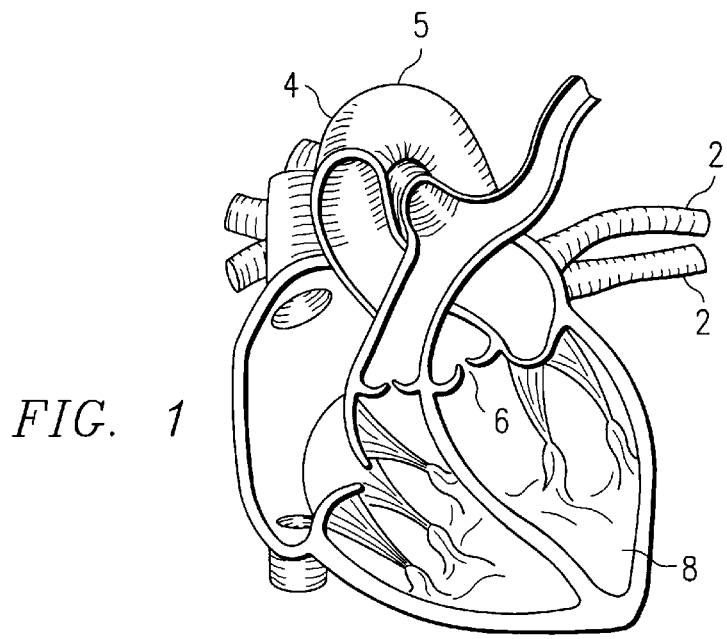
FIG. 1 illustrates a human heart.
Figure 2:
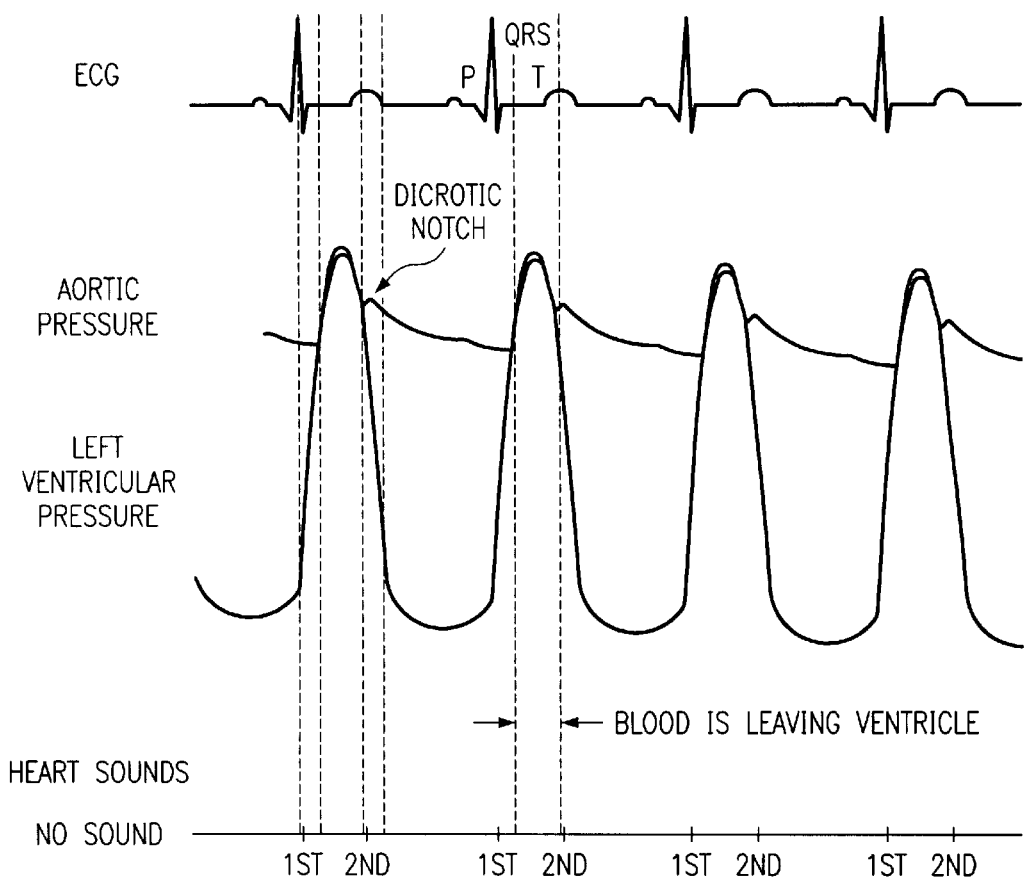
FIG. 2 shows an electrocardiogram and the corresponding aortic pressure for a human heart.

The present invention provides an improved balloon assist catheter that maximizes circulatory effect by precisely timing when the balloon should be inflated. Specifically, the invention comprises a pressure sensor, which is incorporated into the distal tip of the balloon catheter or a guidewire, and an improved circuit for detecting pressure changes. The pressure sensor may, for example, be a strain gauge or fiber optic type sensor.

Small strain gauge type pressure sensors may be made from semiconductor material, such as silicon. These semiconductor devices are generally shaped like a rectangular block, have a strain gauge diaphragm, and include circuitry for providing electrical signals representative of the pressure sensed by the strain gauge to pads that may be connected to external devices. In normal operation, one side of the strain gauge diaphragm is equalized to a reference pressure, such as atmospheric pressure (the reference side), and the other side of the strain gauge diaphragm is exposed to the body tissues or fluids (sensing side). Such semiconductor strain gauge pressure sensors provide high-fidelity pressure measurements.

Alternatively, the pressure sensor may be a fiber optic type sensor. A fiber optic pressure transducer may be made with a small bellows or diaphragm at the tip, structured so that the diaphragm or bellows moves under applied pressure. The device may have one light fiber transmitting light to the mirror and a second fiber receiving the reflected light. Changes in the mirror position, proportional to pressure, cause proportional changes in the amount of reflected light reaching the receiver light fiber. These changes in light intensity are transformed into electrical changes with an external monitoring system. In operation, one side of the diaphragm is exposed to the body tissues or fluids (sensing side) and the other side is exposed to a reference pressure. A typical fiber optic sensor for use with the present invention is available from Camino Laboratories.

In mounting either of these types of sensors to a catheter in previous applications, it has been important to provide a reference pressure to insure high fidelity pressure measurements. The sensor may be mounted to the end of a catheter tip measurement device by using a tubular metal casing, such as a portion of a stainless steel hypodermic needle. With this sturdy metal casing surrounding the sensor, the sensor is isolated from catheter movement and is sensitive only to external sensing pressure. The proximal end of the metal casing may be connected to the catheter body and is open to allow electrical connections from the catheter to reach the pressure sensor. The proximal end is also open to allow venting of the back of the reference side of the strain gauge diaphragm to an external pressure through a lumen in the catheter body. With such prior devices, a window was generally cut into the side of the tubular metal casing. The sensing side of the strain gauge diaphragm of the sensor is left exposed through the window to applied external pressures from body fluids and tissues.

Figure 3A:
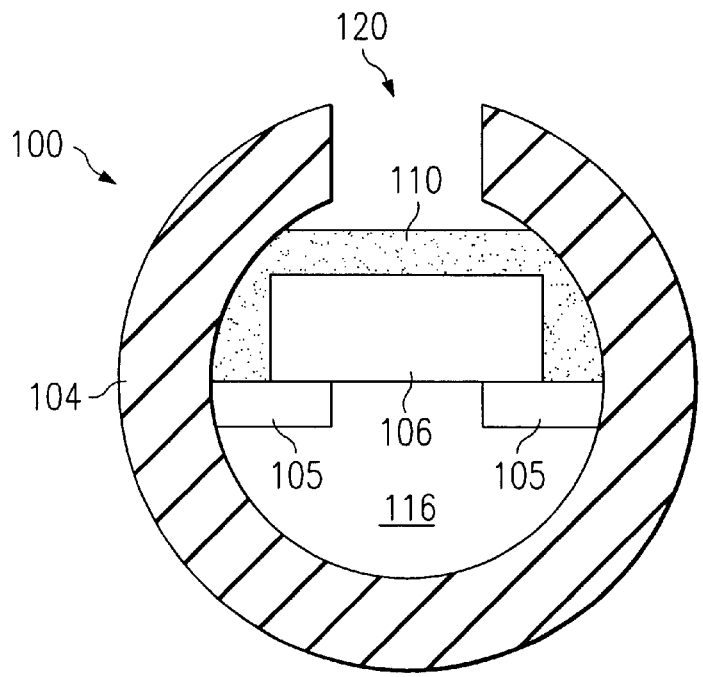
FIGS. 3A and 3B illustrate prior art catheter tip pressure measurement devices.
Figure 3B:
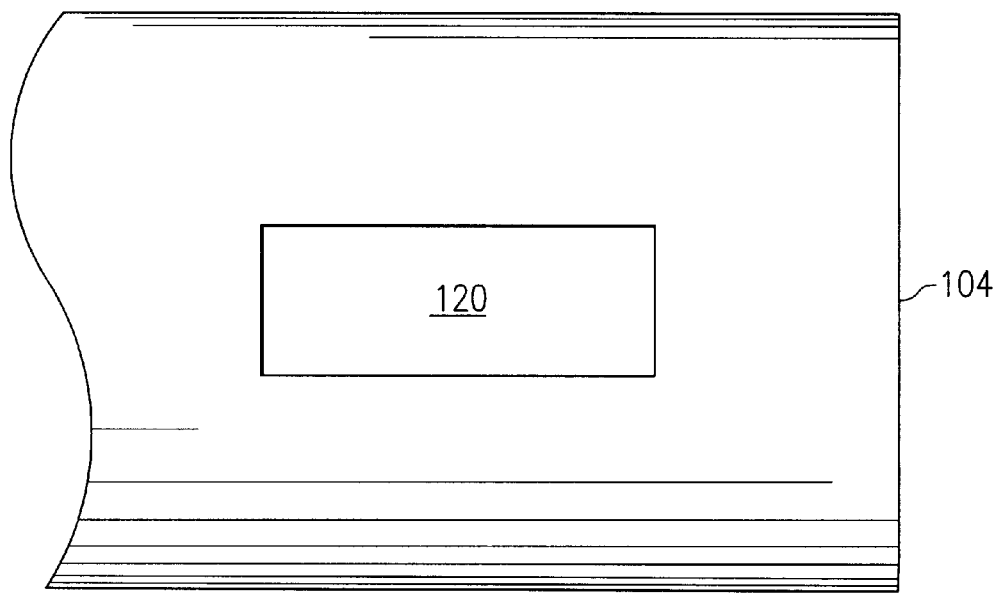

An example of a prior catheter tip pressure transducer device is shown with reference to FIG. 3A (prior art) and FIG. 3B (prior art), which collectively depict the general structure of a prior device 100. FIG. 3A (prior art) depicts an end cross-section view of a tubular metal casing 104 of a prior catheter tip measurement device 100 in the area that the semiconductor pressure sensor 106 is located. FIG. 3B (prior art) depicts a top view of the metal casing 104 showing a window 120 that exposes the sensing side of the diaphragm on the semiconductor pressure sensor 106 to external pressures.

As mentioned above, a window 120 was generally cut out of tubular metal casing 104. Sensor supports 105 were generally attached to the internal walls of tubular metal casing 104. Once semiconductor pressure sensor 106 was placed inside the tubular metal casing 104 on top of sensor supports 105, a protective material 110 was generally applied to keep body tissues and fluids from contacting the semiconductor pressure sensor 106. Such contact could cause electric shock to the surrounding tissues or damage the pressure sensor. One material that was used as the protective material 110 is flexible room-temperature-vulcanizing (RTV) silicone rubber. This protective material 110 was generally applied over the pressure sensor to a thickness of about 0.002 inches.

A venting channel or access region 116 provided a reference pressure to the back of the pressure sensor. Although the shape and size of this vent opening was not significantly important, it generally had to be of a sufficient size to equalize the reference side of strain gauge diaphragm of the pressure sensor to the reference pressure. An opening of approximately 0.002 inches or more in diameter was generally required to achieve this venting requirement. An appropriately sized vent opening was generally easy to achieve, for example, by merely leaving a minor space or channel in the support member underneath the pressure sensor 106. Care had to be taken, however, that the sealant used to cover pressure sensor 106 did not obstruct the venting channel 116. In addition, pressure measurements made within the patient were conventionally compared to atmospheric pressure as a reference pressure, rather than compared to a vacuum.

The present invention achieves a reduced feature size that is not possible with prior designs by eliminating the need for a venting channel for providing an external reference pressure. Further, the present invention eliminates the need for accurately maintaining stable DC pressure levels from the pressure sensor. The present invention does so by providing a unique and advantageous method of detecting changes in pressure detected at a pressure sensor. In particular, the present invention utilizes a detection circuit for detecting the AC component of the signal representing pressure. Thus, for example, the present invention may be used for accurate detection of the dicrotic notch in the aortic pressure without providing a venting channel or requiring a stable DC pressure level to be maintained as with prior systems performing direct pressure monitoring.

Figure 4A:
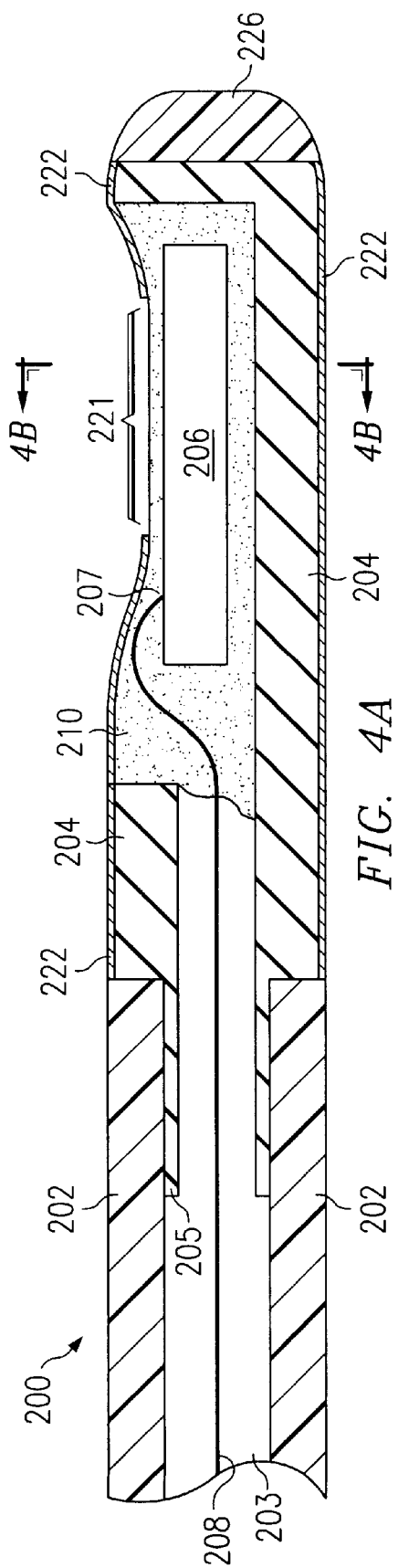
FIGS. 4A, 4B, and 4C show side, top, and cross-section views of a catheter tip pressure measurement device of the present invention.
Figure 4C:
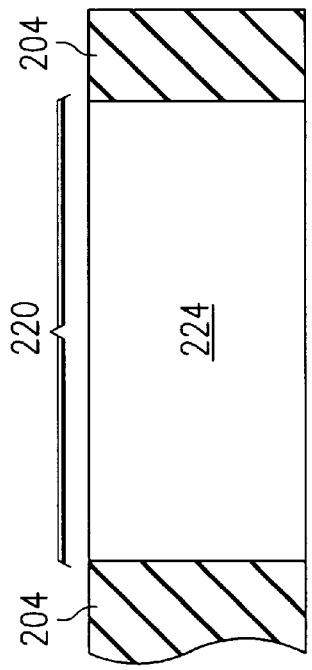
Figure 4B:
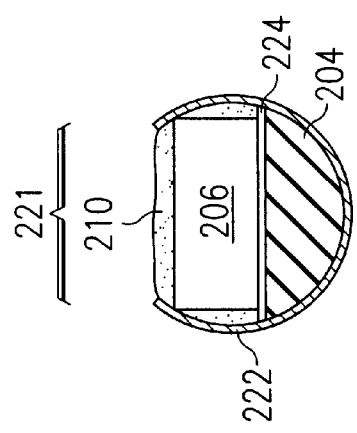

The present invention may be further understood with reference to an embodiment shown in FIG. 4A, FIG. 4B, and FIG. 4C. In particular, FIG. 4A depicts a side cross-section view of a catheter tip pressure sensor 200 according to the present invention. FIG. 4B depicts an end cross-section view along line A—A of FIG. 4A. Finally, FIG. 4C depicts a top view of a mechanical support member 204.

Referring to FIG. 4B, a support member 204 provides mechanical stability for the pressure sensor 206. The support member 204 depicted has a generally planar support surface 224. However, it should be noted that support member 204 may be other shapes and sizes and may have a top width either greater than or less than the width of pressure sensor 206. Preferably, the width of the support surface 224 of support member 204 is approximately the size of the width of the pressure sensor 206 to provide good mechanical stability and a small feature size. Pressure sensor 206 may be attached to support surface 224 with a silicone sealant or an epoxy. Notably, the present invention does not require a venting channel as with prior catheter tip measurement devices such as the one disclosed in applicant's copending application, Ser. No. 08/963,159, which is a continuation-in-part of application Ser. No. 08/744,478. Both are incorporated herein by reference. By eliminating the venting channel, a smaller sized catheter may be obtained.

In the embodiment shown, the support member 204 provides a generally planar support surface for the bottom of the pressure sensor 206. Support member 204 may be constructed by machining a small-diameter tubular metal casing, such as part of a stainless steel hypodermic needle, to remove approximately the top half of the casing to create a support surface in the area where the measurement device will be placed. FIG. 4C depicts such a structure in that a support surface 224 has been created in area 220 of the tubular metal casing 204 to support pressure sensor 206. As also shown in FIG. 4C, the end of the tubular casing may be left in place to provide mechanical strength to the tip of the device. The support member 204 may also be made from non-metal materials, insulating materials, and other materials that provide structural stability. For example, a ceramic material with high dielectric insulating properties could be used to provide strong mechanical support for pressure sensor 206 without the need for external insulation over the ceramic support member.

With reference to FIG. 4A, it is shown that the support member 204 may be attached to a catheter 202 by inserting an annular connecting portion 205 into the end of catheter 202. Annular connecting portion 205 may be created by machining the proximal end of a tubular metal casing. The catheter 202 may be attached to connecting portion 205 in a sealed relation by using an epoxy resin, such as Armstrong A-271. If a metal casing is used for support member 204, the connection may be improved by roughening the metal portions that will contact the epoxy, for example by using sand blasting techniques. In addition, an extremely thin insulating layer 222, which is preferably made of a polyimide material that is relatively easy to seal to metal and other materials, provides superior sealant characteristics to protect the measurement sensors from external fluids. It should be understood, however, that other methods or connecting the support member may be used without departing from the spirit and scope of the present invention.

An epoxy bead 226 may also be placed at the distal end of the device, as shown in FIG. 4A, to close the end of the support member 204 and to provide smooth entry characteristics for the catheter tip measurement device. Electrical connections 208 run from the sensor 206 for connection to the detection circuit of the present invention.

To insulate the semiconductor pressure sensor 206, a flexible insulating material 210 may be applied on top of the pressure sensor 206, as shown in FIG. 4A and FIG. 4B. As with prior devices, this material may be flexible RTV silicone rubber. RTV acts as a good sealant and a good insulator without appreciably affecting the pressure signal transmitted to the diaphragm of the pressure sensor.

To insulate the system from body tissues, an insulating layer 222 is applied to surround the measuring tip of the device as shown in FIG. 4A and FIG. 4B. This insulating layer provides a thin outer sheath that isolates and insulates the electrical measurement components with a drastically reduced feature size than that capable in prior designs. If desired, the insulating layer 222 may be applied to cover only the measuring device or other limited electrical portions of the tip of the device. The insulating layer 222 may be achieved using a thin material that has high dielectric insulating characteristics. In particular, the insulating layer 222 may be made using a polyimide sheath or sleeve. Polyimide is a transparent, relatively inert, biocompatible insulating material available in a variety of thicknesses, including wall thicknesses down to 0.0005 inches. Such a polyimide material is available as polyimide tubing from Micro-Lumen in Tampa, Florida. For example, a polyimide sleeve having an 0.017 inch internal diameter and a 0.018 inch outer diameter may be used as insulating layer 222 for a semiconductor pressure sensor having a width of 0.016 inches. The dielectric strength of such a polyimide sleeve may be 4,000 volts per mil, which will effectively insulate the internal parts of the pressure transducer from the outside world.

A window or opening 221 is provided in the insulating layer 222 over the sensing diaphragm region of semiconductor pressure sensor 206. Unlike RTV silicone rubber, polyimide is a rather stiff material and would significantly reduce the pressure transmissions to the pressure sensor if it also covered the sensing diaphragm. Because the RTV silicone rubber bonds very well with polyimide, a particularly good seal is provided at the interface between the polyimide sleeve and the RTV silicone rubber. For example, an oval shaped window may first be made in a polyimide sleeve for opening 221. The polyimide sleeve may next be slipped over the end of the device as insulating layer 221. RTV silicone rubber may then be applied into the window 221 to cover pressure sensor 206 and create an effective seal with the polyimide sleeve.

The present invention illustrated in FIG. 4A, FIG. 4B, and FIG. 4C may also be used as a guidewire for guiding insertion of catheters. The present invention reduces the size of the guidewire and enables it to be used for applications requiring small diameters.

FIGS. 5A and 5B illustrate side and top views of an embodiment of the present invention in which a pressure sensor 502 is incorporated into the tip of a balloon catheter 500. The balloon catheter 500 is comprised of a catheter body 504 with a balloon 506 surrounding the catheter body 504. A pressure sensor 502 is attached to the catheter tip using an adhesive 508. Wires 510 run through the catheter body 504 for connection to an external circuit. In an embodiment, the pressure sensor 502 may be a semiconductor pressure transducer attached to the catheter tip 512 as described in relation to FIGS. 4A 4C. In an alternate embodiment, the pressure sensor may be a fiber optic type sensor. When a fiber optic sensor is used, wires 510 are replaced with fiber optic cables that are attached to an external device for converting the light signals associated with the fiber optics to an electrical signal representative of the pressure measured at the tip of the balloon catheter.

Figure 6:
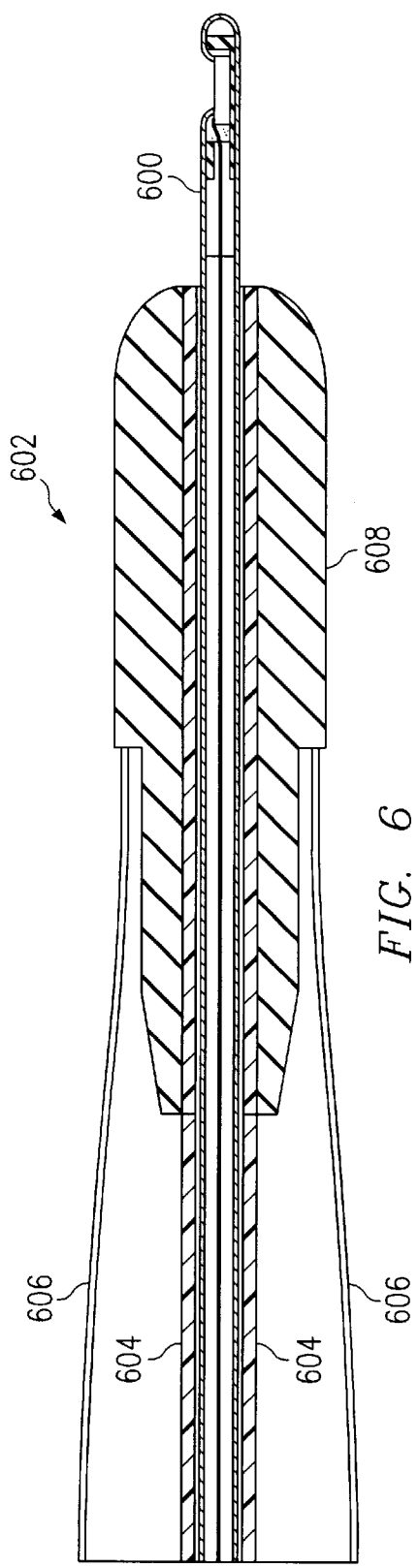
FIG. 6 is a side view of a balloon catheter incorporating a guidewire of the present invention.

FIG. 6 illustrates an alternate embodiment in which the pressure sensor may be incorporated into the tip of a guidewire 600. The balloon catheter 602 includes a catheter body 604 with a balloon 606 surrounding the catheter body 604. Instead of incorporating the pressure sensor into the catheter tip 608 of the balloon catheter as shown in FIGS. 5A and 5B, the pressure sensor is incorporated at the tip of a guidewire as described in relation to FIGS. 4A–4C.

In an embodiment of the invention, a guidewire catheter has been created with a 0.031" O.D. for insertion through a 0.032" lumen in a balloon catheter. The balloon catheter may, for example, be a NarrrowFlex™ Intra-Aortic Balloon catheter available from Arrow. It should be understood, however, that any sized catheter guidewires or catheters may be used without departing from the spirit and scope of the present invention. Instructions for the use and insertion of this balloon catheter are provided in the document "Instruction for Use: Sheathed Intra-Aortic Balloon Catheter Insertion for NarrrowFlex™ IAB's," which is incorporated herein by reference.

In operation, the pressure sensor of the present invention is being used for detecting aortic valve closures in order to timely inflate the balloon of the balloon catheter. According to the present invention, the actual pressure measurement level is not as important as the frequency content of the pressure waveform. The dicrotic notch formed in the aortic pressure waveform typically has a frequency content of approximately 10–15 Hz. By detecting the component of the blood pressure wave form that has a characteristic amplitude and frequency component associated with the dicrotic notch, the present invention may determine when the dicrotic notch occurs (corresponding to closure of the aortic heart valve). Accordingly, a capacitively coupled detection circuit that accurately senses only the AC component of the aortic pressure waveform may be used. By using the capacitively coupled detection circuit, the dicrotic notch can be readily detected. Therefore, the problems associated with the long-term stability of these pressure transducers will not affect the operation of the system because the DC component of the signal representing the aortic pressure waveform is not used for detection purposes. Further, it is not necessary to calibrate the signal levels obtained from the sensor.

Figure 7:
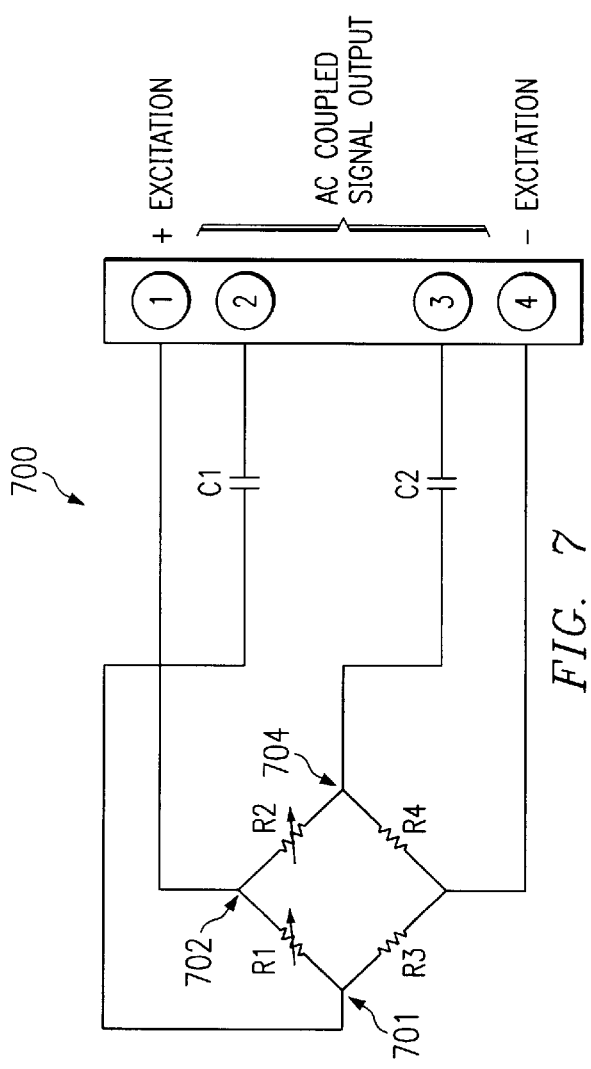
FIG. 7 shows a detection circuit according to the present invention for detecting pressure changes at a pressure sensor.

FIG. 7 depicts an embodiment of a detection circuit of the present invention in which a capacitively coupled detection circuit 700 is used to detect the frequency changes detected by a pressure sensor. The circuit does not accurately detect the DC component of the pressure levels at the pressure sensor; instead, the circuit detects the AC component of the pressure waveform (i.e., the shape and amplitude of the changing portion of the waveform, not the absolute DC level of the detected pressure).

In an embodiment of the invention using a strain gauge type pressure sensor, three electrical connections are provided to interface to an external measurement device. In an embodiment, the pressure transducer includes an active element consisting of two strain gauge transducers, providing resistances R1 and R2, joined together electrically as a center-tapped device. The gauges are implanted on a thin silicon diaphragm that deflects under applied pressure. The configuration of the gauges on the diaphragm is such that as the diaphragm bends, one gauge increases in resistance and the other gauge decreases. In an embodiment of the present invention, the strain gauge transducers are made by Lucas NovaSensor. It should be understood, however, that other transducers may be used without departing from the spirit and scope of the present invention.

In an embodiment of the detection circuit, a constant excitation voltage (5 volts, for example) is applied between terminals 1 and 2. Gauges R1 and R2 convert the aortic pressure changes into resistance changes such that the resistance of gauge R1 increases with increasing aortic pressure and the resistance of gauge R2 decreases with increasing aortic pressure. These gauges make up part of a half-bridge Wheatstone Bridge in which the balancing resistors R3 and R4 are each typically about 800Ω. As the resistances R1 and R2 change to reflect changes in the aortic pressure, the voltage across the middle of the bridge changes. In particular, if the aortic pressure increases, then R1 will also increase, causing the voltage across R3 to decrease. Similarly, an increase in aortic pressure will cause R2 to decrease and the voltage across R4 to increase. Capacitors C1 and C2 (typically each around 0.1 $\mu$F) remove the DC bias from these voltages and provide the inputs to a high input resistance (typically about 100Ω) amplifier connected at terminals 2 and 3. The output of the amplifier provides an output signal corresponding to changes in the aortic pressure. In operation, the output of the amplifier should be operable to provide AC signals in the range of 10 to 15 Hz, which corresponds to the frequency of the signal corresponding to the dicrotic notch. In an embodiment, the amplifier may be an instrumentation amplifier capable of amplifying small differential signals from the capacitively coupled Wheatstone bridge. The output of the amplifier may be used to trigger a valve opening for a pump for the aortic balloon upon detection of the dicrotic notch.

In an alternate embodiment, a fiber optic type sensor may be used with the present invention. The optical information signal from a fiber optic type sensor is translated to an electrical signal. The electrical signal is capacitively coupled through two capacitors to an external amplifier as described in relation to the detection circuit used with the semiconductor pressure sensor. Once again, by using a capacitively coupled detection circuit, the present invention reduces the need for highly accurate sensors with long-term stability that are associated with direct pressure monitoring.

Figure 8:
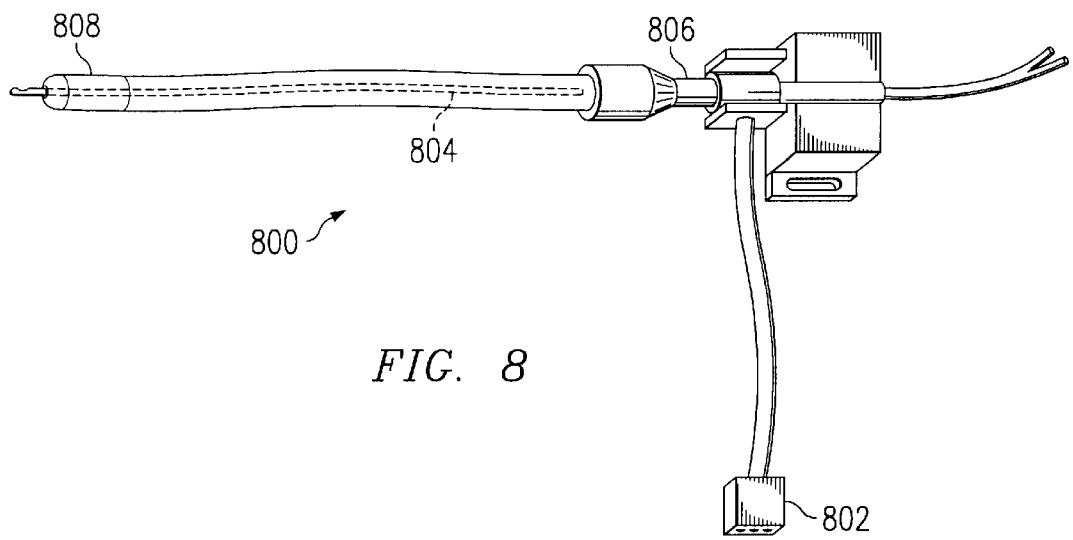
FIG. 8 shows an exemplary embodiment of the present invention in which a balloon catheter and its associated air line are used with an external pressure transducer to reconstruct a high fidelity blood pressure waveform that accurately reflects the mean aortic pressure.

In yet another aspect of the invention, a high fidelity blood pressure waveform may be reconstructed using a pressure sensor and a balloon catheter. Specifically, the signal waveform may be reconstructed by externally adding the mean aortic pressure to the output of the dicrotic notch detector circuit illustrated in FIG. 7. The mean aortic pressure may be measured according to the present invention as illustrated in FIG. 8. Specifically, an external pressure sensor 802 is incorporated into the air line 806 of balloon catheter 800. The balloon catheter is comprised of a catheter body 804 with a balloon 808 surrounding the catheter body 804. In an embodiment, the pressure sensor 802 may be a disposable pressure transducer. An exemplary disposable pressure sensor 802 is a Deltran® disposable pressure transducer, which is readily available from Utah Medical Products Inc. in Midvale, Utah. Although the present invention is illustrated using a Deltran® disposable pressure transducer, it should be understood that other types of pressure transducers, including reusable transducers, may be used without departing from the spirit and scope of the present invention.

In operation, the balloon assist catheter 800 is inserted through the femoral artery, fed through the artery, and located just below the aortic notch within the aorta. After the balloon-assist catheter 800 is inserted, the air line is closed and a small amount of air (on the order of 5 cc's) is inserted with a syringe into the air line in order to create a perfectly limp diaphragm between the internal pressure of the balloon 808 and the pressure in the aorta. Without any air inserted in the balloon, the balloon is completely limp (no pressure) and does not reflect the internal pressure of the aorta. However, when the small amount of air is inserted, the pressure in the balloon (and the airline to the balloon) is identical to the pressure in the aorta. This phenomenon is known as aplanation tonometry in the field of ophthalmology. Specifically, the phenomenon is created when a flexible barrier is flattened between two identical pressures. When inserting air into the balloon, care must be taken not to over inflate the balloon so as to affect the pressure in the aorta. After air has properly been introduced into the balloon, the external pressure sensor 802 will detect the pressure in the balloon, which is now identical to the pressure in the aorta. After obtaining the mean aortic pressure, a high-fidelity aortic waveform may be reconstructed by taking the output of the external pressure transducer 802, which measures the mean pressure, and adding the AC coupled signal output of the dicrotic notch detector circuit illustrated in FIG. 7. Thereafter, the air line is opened and air is introduced into the balloon catheter based on the detection of the dicrotic notch.

Figure 9A:
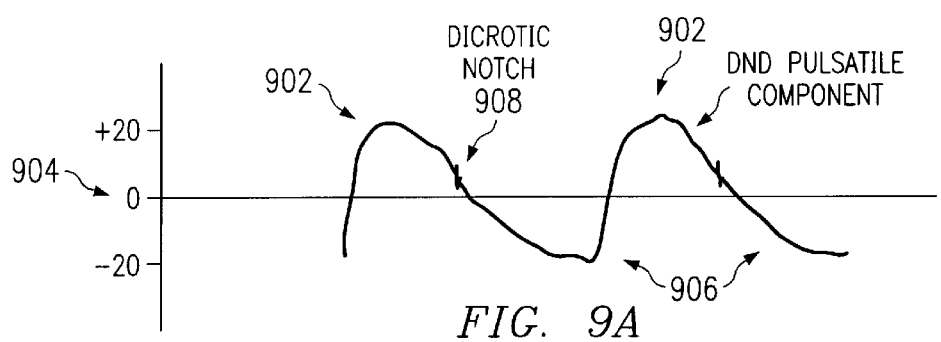
FIGS. 9A and 9B show the high fidelity aortic pulse wave trace and the resulting reconstructed high fidelity blood pressure waveform created using the present invention.
Figure 9B:
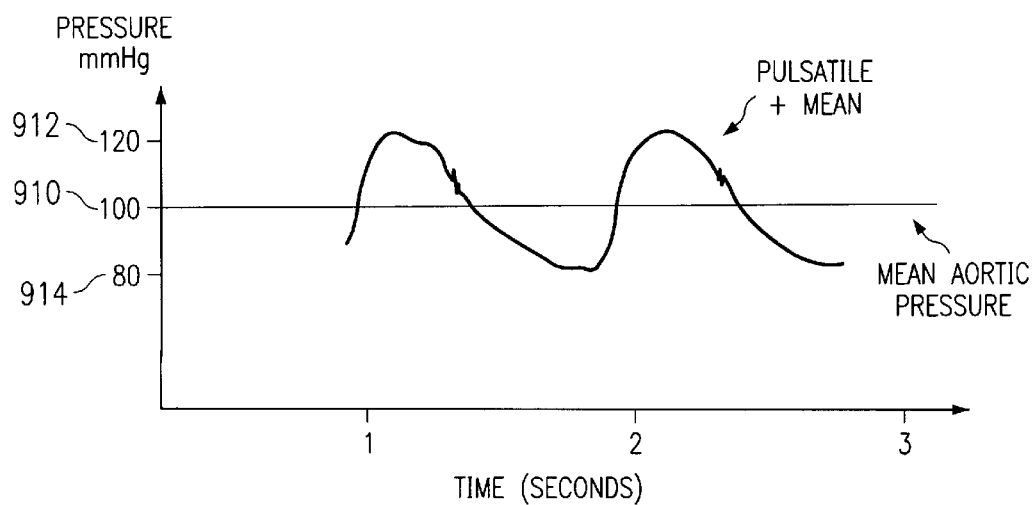

FIGS. 9A and 9B depict the results of measurements of the aortic waveform according to an aspect of the present invention. Specifically, FIG. 9A depicts the capacitively-coupled waveform measured by the detection circuit illustrated in FIG. 7. As shown in FIG. 9A, the component of the waveform 902 above the baseline 904 is equal to the component of the waveform 906 below the baseline 904—resulting in an average pressure reading of "0". As previously described, this waveform accurately reflects the waveform, and in particular, the occurrence of the dicrotic notch 908. However, the recording is inadequate for the measuring the actual levels of pressure in the waveform.

FIG. 9B shows the pressure waveform obtained according to one embodiment of the present invention. In particular, FIG. 9B illustrates a mean blood pressure of 100 mmHg (910), with the capacitively-coupled pressure component superimposed on the mean pressure. On such a combined waveform, the present invention provides an accurate reading of the systolic pressure 912 (120 mmHg) and the diastolic pressure 914 (80 mmHg). In an embodiment of the invention, the mean pressure and the capacitively-coupled waveform may be added together using an oscilloscope that is capable of adding two input channels. In alternate embodiments, the two waveforms may be added using a patient monitor or a computer. It should be understood, however, that any device capable of receiving and adding two waveforms may be used without departing from the spirit and scope of the present invention.

Further modifications and alternative embodiments of this invention will be apparent to those skilled in the art in view of this description Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. In addition, equivalent elements or materials may be substituted for those illustrated and described herein, and certain features of the invention may be utilized independently of the use of other features, all as would be apparent to one skilled in the art after having the benefit of this description of the invention. For example, the present invention may be used to monitor other transient physical phenomena in which the DC component of the signals representing the physical phenomena are not necessary for detection purposes. Pressure sensors may be used at the tip of a catheter for detecting events such as a coughing, a swallowing, or a heart sounds. Although these applications are intended to be illustrative, it would be understood by a person of ordinary skill in the art that the present invention may be used in other applications that require the detection of transient signals representative of pressure changes.

What is claimed is:

1. A system for reconstructing a high-fidelity waveform of the blood pressure in the aorta of a human body, comprising:

a catheter body having a distal end and a proximal end;

a support surface proximate the distal end of the catheter body;

an inflatable balloon surrounding at least a portion of the catheter body;

a pressure sensor supported by the support surface;

a capacitively coupled detection circuit operatively coupled to the pressure sensor for removing DC bias and detecting frequency changes occurring at the pressure sensor; and an external pressure transducer located at the proximal end of the catheter body and operatively coupled for determining the mean pressure within the inflatable balloon.

2. The system of claim 1, further comprising a patient monitor for reconstructing the high-fidelity waveform by adding the output of the capacitively coupled detection circuit and the output of the external pressure transducer.

3. The system of claim 1, further comprising an oscilloscope for reconstructing the high-fidelity waveform by adding the output of the capacitively coupled detection circuit and the output of the external pressure transducer.

4. The system of claim 1, further comprising a computer for adding the output of the capacitively coupled detection circuit and the output of the external pressure transducer.

5. The system of claim 1, wherein the external pressure transducer is disposable.

6. The system of claim 1, wherein the external pressure transducer is reusable.

7. The system of claim 1, wherein the capacitively coupled detection circuit is operable to detect frequency changes corresponding to the dicrotic notch in the aortic pressure.

8. A method for reconstructing a high-fidelity pressure waveform with a balloon catheter used in a heart, comprising:

inserting a balloon catheter having an air line into the aorta of the heart;

closing the airline;

inserting air in the air line to equalize the pressure in the balloon catheter and the aorta;

sensing the aortic pressure changes at the tip of the balloon catheter;

detecting the AC component of the measured aortic pressure changes;

detecting the pressure in the air line in order to determine the mean aortic pressure; and adding the AC component of the measured aortic pressure to the mean aortic pressure to form a high-fidelity pressure waveform.

9. The method of claim 8, wherein the step of detecting the pressure in the air line is performed using a disposable pressure sensor.

10. The method of claim 8, wherein the amount of air inserted in the air line is approximately 5 cc's.

11. The method of claim 8, further comprising displaying the high-fidelity pressure waveform on an oscilloscope.

12. The method of claim 8, further comprising displaying the high-fidelity pressure waveform on a patient monitor.

13. The method of claim 8, further comprising:

detecting the dicrotic notch of the AC component of the measured aortic pressure changes; and inflating the balloon catheter based on the location of the dicrotic notch.

* * * * *